United States Patent
Kelly et al.

(10) Patent No.: US 7,304,405 B2
(45) Date of Patent: Dec. 4, 2007

(54) ELECTRICALLY ISOLATED POWER AND SIGNAL COUPLER SYSTEM FOR A PATIENT CONNECTED DEVICE

(75) Inventors: Clifford Mark Kelly, Windham, NH (US); Scott Newell, Ipswich, MA (US); Tomas Russ, Carlise, MA (US)

(73) Assignee: Draeger Medical Systems, Inc., Andover, MA (US)

( * ) Notice: Subject to any disclaimer, the term of this patent is extended or adjusted under 35 U.S.C. 154(b) by 419 days.

(21) Appl. No.: 10/949,934

(22) Filed: Sep. 27, 2004

(65) Prior Publication Data

US 2005/0047055 A1    Mar. 3, 2005

Related U.S. Application Data

(62) Division of application No. 09/992,696, filed on Nov. 20, 2001, now Pat. No. 6,819,013.

(60) Provisional application No. 60/252,112.

(51) Int. Cl.
*H01B 7/30* (2006.01)

(52) U.S. Cl. ...................................................... 307/147

(58) Field of Classification Search ................. 307/147
See application file for complete search history.

(56) References Cited

U.S. PATENT DOCUMENTS 6,183,417 B1 *    2/2001    Geheb et al. ................ 600/301

* cited by examiner

*Primary Examiner*—Robert L. Deberadinis
(74) *Attorney, Agent, or Firm*—Jack Schwartz & Associates, PLLC

(57) ABSTRACT

An electrically isolated, combined power and signal coupler, for a patient connected device, is disclosed. A docking station and a portable device, capable of docking with the docking station each include a power coupler and an electrically isolated data transducer. The respective power couplers include a magnetically permeable element including a central pole and a peripheral pole and a printed circuit board with an opening through which the central pole protrudes. The printed circuit board includes windings surrounding the central pole opening: a primary winding in the docking station and a secondary winding in the portable device. When the portable device is docked with the docking station, the magnetically permeable element in the portable device and the magnetically permeable element in the docking station are arranged to form a magnetic circuit, and the data transducer in the portable device and the data transducer in the docking station are arranged to exchange data.

18 Claims, 3 Drawing Sheets

System

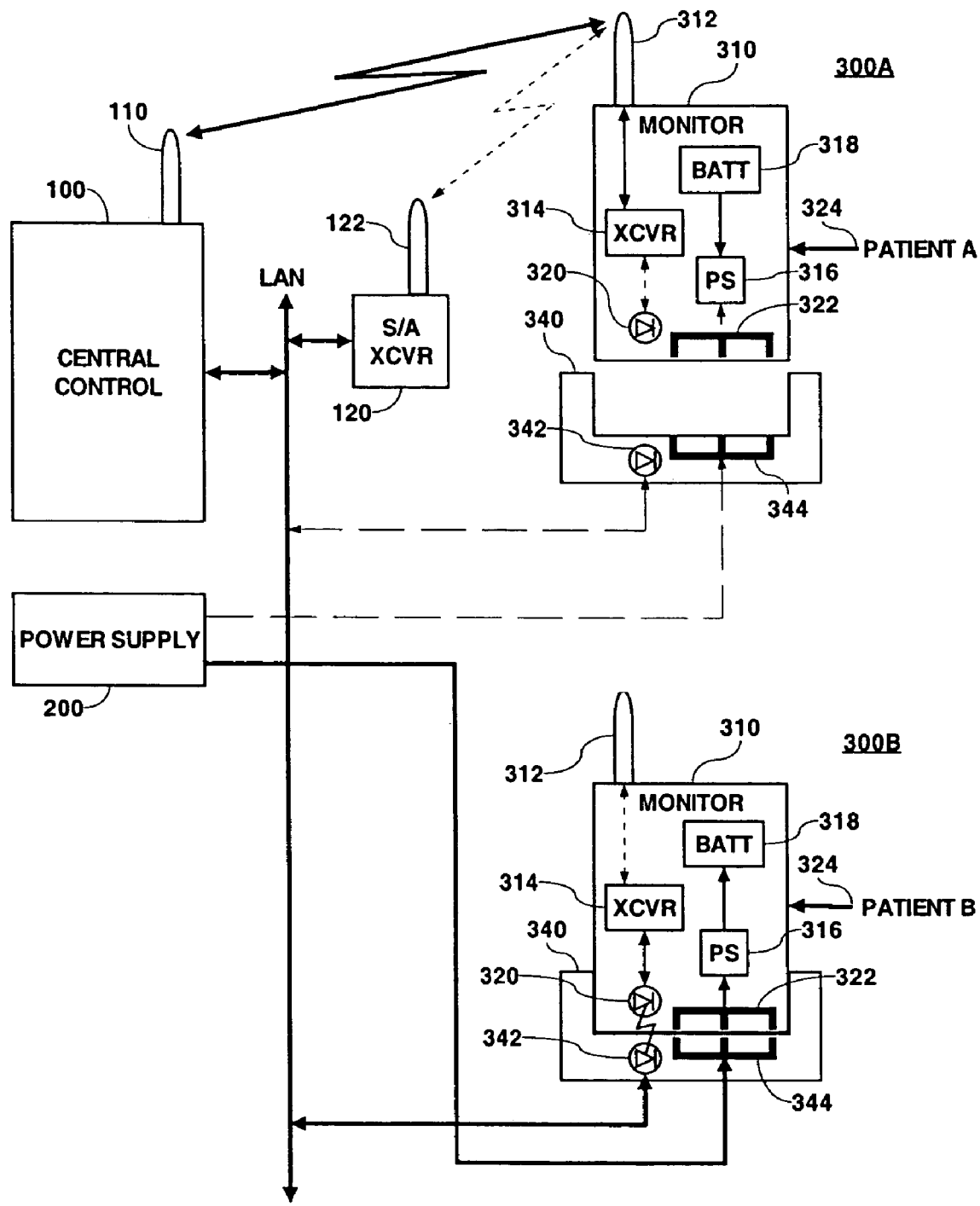
Fig. 1 - System

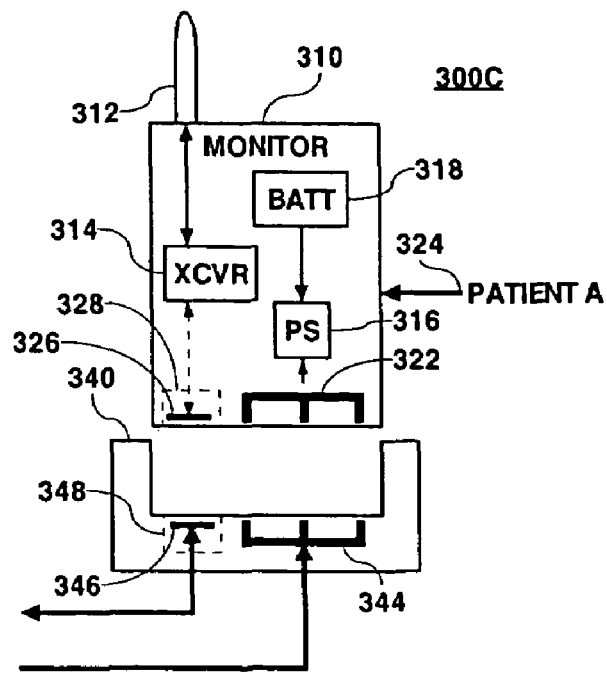
Fig. 2 – Alternate transmission medium
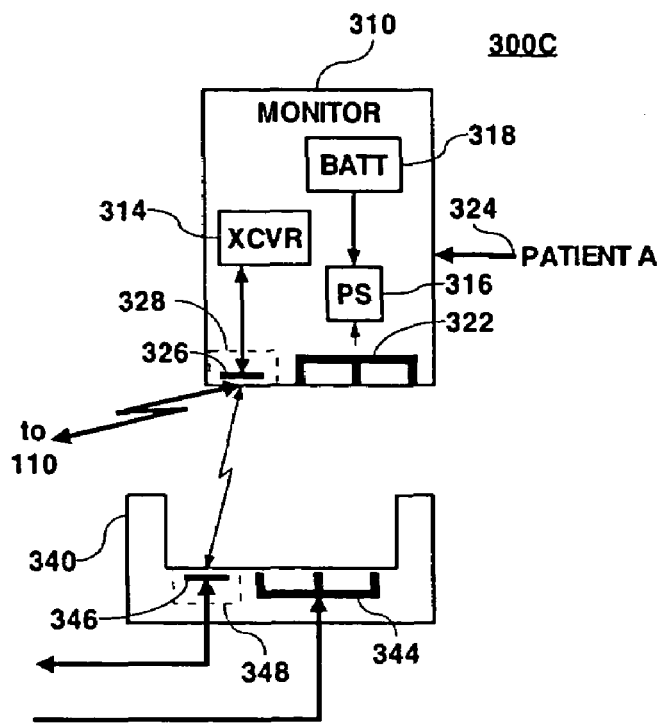
Fig. 3 –Alternative 2 transmission medium

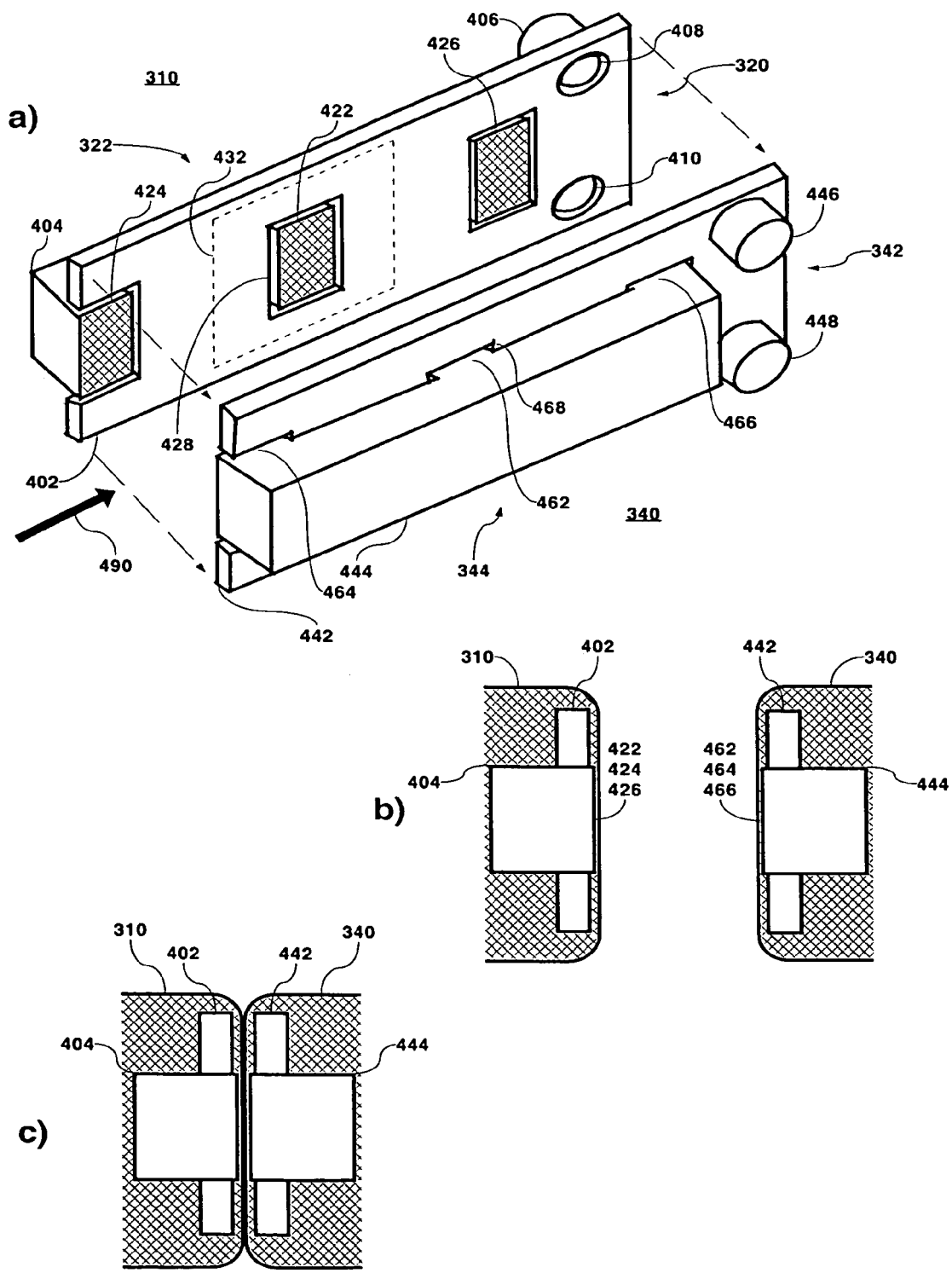
Fig. 4 – Detailed view

ELECTRICALLY ISOLATED POWER AND SIGNAL COUPLER SYSTEM FOR A PATIENT CONNECTED DEVICE

CROSS-REFERENCE TO RELATED APPLICATIONS

This application is a Divisional application No. 09/992,696, filed Nov. 20, 2001 claiming priority from provisional application 60/252,112 filed Nov. 20, 2000.

FIELD OF THE INVENTION

The present invention relates to a power and signal coupler for a portable medical monitoring device designed to be connected to a patient in a medical environment.

BACKGROUND OF THE INVENTION

Monitoring systems for patients in a medical environment have long been known. These monitors include electrodes which are designed to be attached to the patient. The electrodes receive electrical signals which represent physiological functions in the patient. Some form of indication of the values of those signals is then displayed. For example, an electrocardiogram (ECG) system includes electrodes designed to be attached to the patient on the chest, inter alia. These electrodes receive electrical signals indicative of the instantaneous operation of the patient's heart. Images representing waveforms related to the ECG electrode signals are displayed on a display device for a doctor to analyze.

Recently, it has been recognized that, in a hospital setting, there are advantages to maintaining all monitoring data gathered from patients, and other data gathered about those patients, such as lab results etc., in a central location. Such an arrangement would allow patient information to be available anywhere in the hospital. Such an arrangement would also permit patient information, possibly derived from monitoring equipment, to be received and stored in the central location from anywhere in the hospital.

In the past, monitoring equipment was maintained at one fixed location, e.g. an examining room. Patients requiring that type of monitoring were moved to the room containing the monitoring equipment, and connected to the monitoring equipment. The monitoring equipment was plugged into the AC power socket at the fixed location. In addition, a direct wired connection between the monitoring equipment at this fixed location and the central storage location was maintained, making it easy to transfer monitoring data to the central location to be stored. However, recently, it has been recognized that in some cases it is important to maintain monitoring of a patient at all times; even those times when the patient is in transit, e.g. among patient room, examining room, operating room, etc. This requires that monitoring equipment be portable. By this method, the monitoring equipment may be transported along with the patient from one location to another. There are two aspects to enabling portability of monitoring equipment: first is supplying power to the monitoring equipment; second is maintaining a data link between the monitoring equipment and the central location, while it is in transit with the patient.

The aspect relating to providing power to the monitoring equipment was solved by including batteries in the monitoring equipment. One skilled in the art will understand that batteries require charging, and that patients are in transit a small fraction of the time. Current portable monitoring equipment includes fixed docking stations in all appropriate fixed locations, such as operating rooms, examining rooms and patient rooms. When a patient is in one of these locations, the portable monitoring equipment is inserted into the docking station at that location. These docking stations are connected to the AC power at that location, and provide charging current for the batteries in the monitoring equipment. This permits the batteries to maintain their charge. When a patient is moved, the monitoring equipment, with a charged battery, is removed from the docking station, and transported with the patient until another docking station is available.

Because the docking station is connected to AC power, and because it is well known that it is dangerous for electrical power to be applied directly to a patient, especially above the waist, standards-have been developed to ensure that all electrical power is isolated from electrodes intended to be attached to the patient. This has required that battery charging current be provided to the portable monitoring equipment without a direct electrical connection between the AC power socket and the portable monitoring equipment. This has been done using the known technique of split transformers in the form of a bobbin in the monitoring equipment which surrounds a magnetic core in the docking station when the equipment is docked. The AC current induces an alternating magnetic flux around the magnetic core in the docking station, which, in turn, induces a current in the bobbin in the monitoring equipment when docked. This current, in turn, provides operating power for the monitoring equipment and also maintains the batteries charged, all in a known manner. Operating efficiencies of around 60% may be obtained using this known system.

The aspect relating to maintaining a data link when the monitoring equipment is docked was solved by providing a wireless, e.g. radio frequency (RF), link for transmitting monitoring data from the monitoring equipment to the central location. Each piece of monitoring equipment includes an RF transceiver and antenna. Each docking station also includes a corresponding RF transceiver and antenna. In addition, free-standing antennae and transceivers are located throughout the hospital, in particular at locations where patients would be transported, e.g. halls, etc. Each of the transceivers in the docking stations and the free standing locations is connected by a wired connection to the central location. Using RF communications between the docking station and the monitoring equipment further provides electrical isolation.

When a patient is in a fixed location, and the monitoring equipment is placed in a docking station, the docking station receives the RF signal from the monitoring equipment and transmits the data to the central location via its wired connection. When a patient is in transit from one fixed location to another, the free standing antennae/transceiver locations receive the RF signal from the monitoring equipment and transmit the data to the central location. This provides the ability to monitor a patient continuously.

However, there are locations in which continuous RF transmissions from the monitoring equipment may cause problems and must be carefully planned for. For example, in operating rooms, electro-cautery machines use RF energy to cut tissue and coagulate blood during surgery. This instrument causes an unpredictable amount of RF energy and could possibly interfere with the RF link of the monitoring equipment. However, it is in this environment that it is most important that no monitoring data be lost or corrupted.

Monitoring equipment which is portable, in which power efficiency is higher than 50%, and in which potential RF interference is minimized is desirable.

BRIEF SUMMARY OF THE INVENTION

In accordance with principles of the present invention, an electrically isolated combined power and signal coupler for a patient connected device, is disclosed. A docking station, and a portable device capable of docking with the docking station, each include a power coupler and an electrically isolated data transducer. The respective power couplers include a magnetically permeable element including a central pole and a peripheral pole and a printed circuit board with an opening through which the central pole protrudes. The printed circuit board includes windings surrounding the central pole opening: a primary winding in the docking station and a secondary winding in the portable device. When the portable device is docked with the docking station, the magnetically permeable element in the portable device and the magnetically permeable element in the docking station are arranged to form a magnetic circuit, and the data transducer in the portable device and the data transducer in the docking station are arranged to exchange data.

BRIEF DESCRIPTION OF THE DRAWING

In the drawing:

FIG. 1 is a block diagram of a monitoring system including a central location, docking stations and portable monitoring devices; and FIG. 2 and FIG. 3 are block diagrams of a monitoring device illustrating an arrangement for using alternative transmission media; and FIG. 4 is an assembly diagram illustrating the power and data transmission apparatus for a monitoring system as illustrated in FIG. 1.

DETAILED DESCRIPTION OF THE INVENTION

FIG. 1 is a block diagram of a monitoring system including a central location, docking stations and portable monitoring devices. FIG. 1 illustrates a plurality (300A and 300B) of portable monitoring devices 310 and docking stations 340 each coupled to a central controller 100 and central power supply 200. Each monitoring device 310 includes electrodes 324 intended to be attached to a patient (PATIENT A and PATIENT B).

Each portable monitoring device 310 includes an RF antenna 312. A bidirectional terminal of the RF antenna 312 is coupled to a corresponding terminal of a transceiver 314. The transceiver 314 is coupled (not shown) to other circuitry (also not shown) in the monitoring device 310. Each portable monitoring device 310 also includes a battery 318. The battery 318 is coupled to a power supply 316. The power supply 316 is also coupled (not shown) to the other circuitry in the monitor 310, all in a known manner. The design, operation and interconnections of the other circuitry discussed above is well known to one skilled in the art, is not germane to the present invention and will not be described in detail below.

An optical transducer 320 in the illustrated embodiment represents a wireless two-way full duplex optical transducer. One skilled in the art will understand that this transducer may include a light emitting diode (LED) for transmitting and a photo-transistor for simultaneously receiving optical signals. A bidirectional terminal of the optical transducer 320 is coupled to a corresponding terminal of the transceiver 314. Data terminals (not shown) of the transceiver 314 are connected to other circuitry (also not shown) in the monitoring device 310.

The monitoring device 310 also includes a secondary 322 of a split transformer. The secondary 322 is coupled to an input terminal of the power supply 316. The structure and operation of the split transformer 316 will be described in detail below.

Each docking station 340 includes an optical transducer 342 representing a wireless two-way full duplex optical transducer. The optical transducer 342 corresponds to the optical transducer 320 in the monitoring device 310, and is arranged physically so that full duplex communication may be carried on between the corresponding optical transducers 320 and 342 when the monitoring device 310 is docked in the docking station 340.

The docking station 340 also includes a primary 344 of the split transformer. The primary 344 corresponds to the secondary 322 of the split transformer in the monitoring device 310, and is arranged so that a complete transformer is formed, and electrical power transferred, when the monitoring device 310 is docked in the docking station 340.

FIG. 1, also illustrates a central controller 100. The central controller 100 includes a bidirectional data terminal coupled to a local area network (LAN). This LAN connects with various workstations (not shown) within the hospital and also may include a bridge (also not shown) to a wide area network (WAN) such as, for example, the internet. The optical transducers 342 in the plurality 340 of docking stations are bidirectionally coupled to the LAN. Although the optical transducers 342 are illustrated as being coupled to the central controller 100 via the LAN, one skilled in the art will understand that respective bidirectional signal lines may be coupled directly between the optical transducers 342 in each of the plurality of docking stations 340 and corresponding bidirectional terminals on the central controller 100. These respective signal lines may then be used to communicate directly between docking stations 340 and the central controller 100.

The central controller 100 also includes an RF antenna 110. This RF antenna 110 is capable of communicating with the respective RF antennae 312 of the monitoring devices 310 via radio transmission in a known manner. Although illustrated as a single antenna 110, one skilled in the art will understand that multiple antennae, distributed throughout the hospital, may all be connected to the central controller 100. For example, a standalone transceiver 120 is coupled to the LAN. The standalone transceiver 120 includes an RF antenna 122 capable of exchanging data with the portable devices 310, as illustrated in phantom in FIG. 1. As described above, these standalone transceivers may also be connected to the central controller 100 via respective direct connections. Such standalone transceivers may be placed throughout the hospital for communicating with the portable monitoring devices 310 while undocked and in transit.

A power supply 200 is coupled to the respective primaries 344 in the plurality of base stations 340. Although illustrated as a separate element in FIG. 1, the standard distributed AC power system may be used for providing power to the plurality of primaries 344 in the plurality of base stations 340.

In operation, the monitoring devices 310 operate in one of two states: docked or undocked. The monitoring device 310 and docking station 340 pair in the upper part of the figure, 300A, are in the undocked condition, and the monitoring device 310 and docking station 340 pair in the lower part of the figure, 300B, are in the docked condition. In general, when a monitoring device 310 is docked, data communications takes place through the optical transducers 320,342 and power is supplied to the monitoring device 310 through the split transformer 344,322. When a monitoring device is undocked, data communications takes place through the RF antenna 312 and power is supplied from the battery 318.

In 300A (undocked), the connection between the optical transducer 320 and the transceiver 314 is illustrated in phantom to indicate that it is currently inoperative, while the connection between the antenna 312 and the transceiver 314 is indicated by a solid line to indicate it is operating. The zigged line between the antenna 110 on the central controller 100 and the antenna 312 on the monitoring device 310 illustrates that an RF link is being maintained between the monitoring device 310 and the central controller 100. Similarly, the connection between the secondary 322 of the split transformer and the power supply 316 is illustrated in phantom to indicate that it is currently inoperative, while the connection between the battery 318 and the power supply 316 is indicated by a solid line with an arrow to indicate that power is being transferred from the battery 318 to the power supply 316. The data connection between the optical transducer 342 in the docking station 340 and the LAN, and the power connection between the power supply 200 and the primary 344 of the split transformer are illustrated in phantom to illustrate that they are currently inoperative.

In 300B (docked), the connection between the antenna 312 and the transceiver 314 is illustrated in phantom to indicate that it is currently inoperative, while the connection between the optical transducer 320 and the transceiver 314 is indicated by a solid line to indicate it is operating. The zigged line between the optical transducer 342 in the docking station 340 and the optical transducer 320 in the monitoring device 310 illustrates that an optical link is being maintained between the monitoring device 310 and the central controller 100. Similarly, the connection between the secondary 0.32.2 of the split transformer and the power supply 316 is illustrated by a solid line to indicate that it is currently operating. The connection between the battery 318 and the power supply 316 is indicated by a solid line with an arrow to indicate that charging power is being transferred from the power supply 316 to the battery 318. The connections between the LAN and the optical transducer 342 in the docking station 340 and between the power supply 200 and the primary 344 of the split transformer are illustrated as solid lines to indicate they are operative. There is no zigged line between the antenna 312 of the monitoring device 310 and the antenna 110 of the central controller 100 which indicates that there is no RF communications taking place.

One skilled in the art will understand that the central controller 100 will be in communications with many monitoring devices 310 simultaneously, through the LAN and/or through respective hardwired connections (not shown) to docking stations 340 in which the monitoring devices 310 are docked, and/or through wireless RF links to undocked monitoring devices 310. Any of the known techniques for carrying on simultaneous communications, such as time division multiplexing, frequency division multiplexing, packetized communication, or any combination of such techniques may be used to provide this simultaneous communications. For example, various protocols are in general usage for network communications among a plurality of network nodes. More specifically, such protocols include, among many others: internet protocol (IP), universal serial bus (USB), I.E.E.E. newtork protocol. Any of these known protocols may be used to communicate between the plurality of monitoring devices 310 and the central controller 100 via the LAN. These same protocols may be also used for wireless RF communications between undocked monitoring devices 310 and the antenna 110 of the central controller 100, directly or through standalone transceivers 120 connected to the central controller 100 via the LAN or through respective hardwired connections.

Known circuitry in the monitoring device 310 and the docking station 340 detects when the monitoring device 310 is docked with the docking station 340. In one embodiment, because electrical power is transferred only when the monitoring device 310 is docked with the docking station 340, such circuitry in the docking station 340 may detect a load (secondary 322) attached to the primary 344 and corresponding circuitry in the monitoring device 310 may detect the presence of power at the secondary 322. For another example, because data will be exchanged via the optical transducer pair 320,342 only when the monitoring device 310 is docked with the docking station 340, such circuitry in the docking station 310 may detect the presence of data from the optical transducer 320 and corresponding circuitry in the docking station 340 may detect the presence of data from the optical transducer 342.

When the docking station 340 detects that a monitoring device 310 is docked, the central controller 100 begins communicating through the LAN with the optical transducer 342 in the docking station 340. Simultaneously, when the monitoring device 310 detects that it has been docked, the transceiver 314 is connected to the optical transducer 320, and communications is initiated via the optical transducer pair 320,342 through the LAN, with the central controller 100. More specifically, the transceiver 314 in the monitoring device 310 generates data in the network protocol used by the LAN, i.e. IP packets. The packetized data is then passed through the optical transducer pair 320,342 to the LAN. The central controller 100, in turn, receives the IP packets from the LAN and extracts the data. This data is then processed by the central controller 100. For example, patient monitoring data is stored in the central location. Concurrently, data from the central controller 100 meant for the monitoring device 310 is packetized and placed on the LAN. The packetized data is received by the monitoring device 310 via the optical transducer pair 342,320. The transceiver 314 extracts the data and controls the operation of the monitoring device 310 in the manner specified by the received data. For example, monitoring parameters may be set or changed by the central controller 100.

At the same time, when it is detected that the monitoring device 310 is docked in the docking station 340, power from the secondary 322 of the split transformer powers the circuitry in the monitoring device 310, including charging the battery 318.

When the docking station 340 detects that a monitoring device 310 has been undocked, the central controller 100 is notified and it begins communicating through the RF antenna 110. Concurrently, when the monitoring device 310 detects that it has been undocked, the transceiver 314 is connected to the RF antenna 312, and communications is initiated via the RF link to the central controller 100. As described above, the transceiver 314 generates the data in the selected network protocol, i.e. IP packets. This packetized data is transmitted to the central controller 100 via the wireless RF antenna 110. The central controller 100 receives the IP packets, extracts the data and processes the data, e.g. stores the patient monitoring data. The central controller 100 may also generate IP packets of data meant for the monitoring device 310. The central controller 100 transmits this packetized data to the antenna 312 of the monitoring device 310 via the wireless RF antenna 110. The transceiver 314 in the monitoring device 310, in turn, receives the IP packets, extracts the data and controls the operation of the monitoring device 310 in response.

Alternatively, the standalone transceiver 120 may communicate via a wireless RF signal with the monitoring device 310. In this case, the antenna 312 of the monitoring device 310 transmits the packetized patient monitoring data to the antenna 122 of the standalone transceiver 120, as described above. The standalone transceiver 120 receives this packetized data and places it on the LAN. The central controller 100 receives the IP packets from the LAN, extracts the data and processes it in the desired manner. The central controller 100, in turn, places packetized data meant for the monitoring device 310 on the LAN. The standalone transceiver 120 receives the packetized data and transmits it to the antenna 312 of the monitoring device 310. The transceiver 314 in the monitoring device 310 receives the packets, extracts the data from the received packets and controls the operation of the monitoring device in response.

In addition, power from the battery 318 powers the circuitry in the monitoring device 310 when the monitoring device is undocked.

In the embodiment illustrated in FIG. 1 and described above, the transmission medium changes from when the monitoring device 310 is docked (optical) to when it is undocked (RF). However, one skilled in the art will understand that it is possible to share the same transmission medium in both modes. FIG. 2 illustrates a monitoring device 310 with an alternate means for communicating with the central controller 100 when docked. In FIG. 2, the transceiver 314 in the monitoring device 310 is coupled to an RF antenna 326 physically arranged to be adjacent to the docking station 340 when it is docked. The docking station 340 includes a corresponding RF antenna 346 physically arranged to be adjacent the RF antenna 326 in the monitoring device 310 when it is docked. These antennae 326 and 346 may be small and are arranged to be close to each other. A shield 328, illustrated by a dotted line, in the monitoring device 310 surrounds the antenna 326, and a corresponding shield 348 in the docking station 340 surrounds the antenna 346. The shields 328 and 348 are physically arranged to cooperate when the monitoring device 310 is docked in the docking station 340 to completely shield the antennae 326 and 346 so that they do not radiate to the surrounding area, and so that RF interference in the surrounding area, such as may be generated by surgical equipment, does not produce interference in the communication between them.

In this manner, the central controller 110 may use a common RF transceiver for both docked and undocked monitoring devices 310. When docked, the RF antenna pair 326 and 346 are used, and when undocked, the RF antenna pair 110 and 312 are used. One skilled in the art will understand that the signal level from an RF antenna 346 in a docking station 340 will be stronger than that from the broadcast antenna 110. One skilled in the art will understand that attenuators and/or amplifiers may be necessary to enable use of an RF transceiver with normal dynamic range in the central controller 100.

FIG. 3 illustrates a monitoring device 310 with another alternate means for communicating with the central controller 100 when docked and undocked. In FIG. 3, the monitoring device 310 does not include an antenna 312 as in FIG. 1 and FIG. 2. Instead, in FIG. 3, the embedded antenna 326 operates as the RF antenna both when the monitoring device 310 is docked, as in FIG. 2, and also when the monitoring device 310 is undocked, as illustrated by the thick zigged line in FIG. 3. As in FIG. 2, when the monitoring device 310 is docked, the shields 326 and 346 cooperate to completely shield the antennae 326 and 346 from the surrounding area. However, in FIG. 3, when the monitoring device 310 is undocked, the shields 328 and 348 part and the antenna 326 is able to transmit to the surrounding area. That is, the antenna 326 is able to transmit to the antenna 110 on the central location or any of the plurality of free standing antennae in the hospital, as described above. Furthermore, the antenna 346 in the docking station 340 is able to act as one of the standalone antennae (such as 122—FIG. 1) receiving RF signals from the antenna 326 in the monitoring device 310. Therefore, the antenna 326 in the monitoring device 310 is able to communication with the antenna 346 in the docking station 340 even when it is undocked. This is illustrated in FIG. 3 by a thin zigged line.

One skilled in the art will understand that additional reliability may be obtained by using redundant transmission media. For example, a monitoring device 310 and docking station 340 may include both optical transducers 320 and 342, as illustrated in FIG. 1, and also RF antennae 326 and 346 as illustrated in FIG. 2 and FIG. 3. In operation, both media are used to transmit data between the monitoring device 310 and the docking station 340 concurrently.

FIG. 4a is an assembly diagram illustrating apparatus for implementing the split transformer 322,344 and corresponding optical transducers 320,342 illustrated in FIG. 1. In FIG. 4a, the assembly in the upper left portion represents elements contained in the monitoring device 310 and the assembly in the lower right portion represents elements contained in the docking station 340. In the actual implementation, these two assemblies are molded into the sides of the monitoring station 310 and docking station 340, respectively, in locations such that, when the monitoring device 310 is docked in the docking station 340, they are aligned in a manner to be described in more detail below.

The assembly in the docking station 340 includes a portion 344 forming the primary of the split transformer 322,344. The primary 344 includes a magnetically permeable element, which in the illustrated embodiment is a ferrite armature 444 having a central pole 462 and two peripheral poles 464 and 466, respectively. The primary 344 further includes a printed circuit board (PCB) 442 having an opening 468 through which the central pole 462 protrudes. The PCB 442 also includes other openings through which the peripheral poles 464 and 466 protrude. This PCB 442 is preferably a multi-layer PCB having on the order of 10 or more layers. Windings are fabricated in the PCB 442 in the area immediately surrounding opening 468 for the central pole 462 in a known manner by laying traces (not shown to simplify the figure) around the central core and providing feed-throughs from layer to layer to form a cylinder of windings. This cylinder corresponds to a layer of a traditional, bobbin wound transformer winding when the gaps in each winding ring are connected together, serially. Additional cylinders of windings, around the central pole 462, may be formed in the same manner. Many more winding turns can be realized in this manner over a spiral winding on a single layer. The windings in the PCB 442 form the primary winding of the split transformer 344.

Similarly, the assembly in the monitoring device 310 includes a portion 322 forming the secondary of the split transformer 322,344. The secondary 322 includes a magnetically permeable element, e.g. a ferrite armature 404 having a central pole 422 and two peripheral poles 424 and 426, respectively. The faces of these poles are shown cross-hatched in FIG. 4a. These poles 422,424,426 correspond to the central pole 462 and peripheral poles 464 and 466, respectively, in the primary 344 of the split transformer and are fabricated so that the faces of these poles 422,424,426 align with the faces (not shown) of the corresponding poles 462,464,466 in the primary 344 when the monitoring device 310 is docked in the docking station 340. The secondary 322 further includes a PCB 402 having an opening 428 through which the central pole 422 protrudes. The PCB 402 includes other openings through which the peripheral poles 424 and 426 protrude. Windings are fabricated in the PCB 402 in the area, indicated in phantom as 432, immediately surrounding opening for the central pole 422 in the manner described above. The windings in the PCB 402 form the secondary winding of the split transformer 322.

One skilled in the art will recognize that the magnetic cores 404 and 444 illustrated in FIG. 4*a* are matching E-cores. As is well known, in an E-core a winding around a central pole forms one magnetic-field-pole and the outside two poles surrounding the central pole form the other magnetic-field-pole. In FIG. 4*a*, the center poles 422 and 462 correspond to the central poles in the respective E-cores and the peripheral poles 426,466 and 424,464 correspond to the outside poles in the respective E-cores. One skilled in the art will further recognize that, although the PCBs 402, 442 must surround the central poles 422 and 462 in order to provide the secondary and primary windings respectively, there is no requirement for the PCBs 402,442 to surround the peripheral poles 424,464 and 426,466 for electrical or magnetic reasons.

In addition, the skilled practitioner will recognize that the magnetic armatures 404,444 may be fabricated from any magnetically permeable material, including iron or laminated iron. However, the efficiency of the power transferred from primary 344 to secondary 322 will vary with the selected magnetic material, among other factors.

In a preferred embodiment, the faces of the poles 422, 424,426 in the secondary 322, and the faces of the poles 462,464,466 in the primary 344 are fabricated very close to the surface of the housing of the monitoring device 310 and docking station 340, respectively, so that only a thin layer of non-magnetic nonconductive material, e.g. plastic, covers them. FIG. 4*b* illustrates an end view of the split transformer illustrated in FIG. 4*a* looking in the direction of the arrow 490 when the monitoring device 310 is undocked from the docking device 340. In FIG. 4*b*, the left hand side represents the monitoring device 310 and the right hand side represents the docking station 340. In FIG. 4*b*, the cross-hatched area represents an encapsulating material, such as plastic. The ferrite core 404 in the monitoring device 310 and the ferrite core 444 in the docking station 340 are fabricated so that a very thin layer of the plastic is deposited atop the faces of the poles 422,424,426 and 462,464,466. In the illustrated embodiment, the thickness of the plastic over the faces of the poles is 10 to 15 thousands of an inch. The PCBs 402 and 442 provide the secondary and primary windings, respectively, as described above. FIG. 4*c* illustrates an end view of the split transformer when the monitoring device 310 is docked with the docking station 340. In a docked position the thickness of the plastic between the faces of the poles of the respective ferrite cores 404 and 444 totals 20 to 30 thousands of an inch. This provides a very high degree of magnetic coupling and correspondingly high magnetic and power transfer efficiency.

FIG. 4*a* also illustrates the apparatus for implementing the optical transducers 320 and 342. The optical transducer 342 in the docking station 340 includes an optical transmitter, in the form of a light emitting diode (LED) 446, and an optical receiver, in the form of a photo-transistor 448. The optical transducer 320 in the monitoring device 310 also includes an optical transmitter in the form of an LED 410 and an optical receiver in the form of a photo-transistor 408. These LEDs and photo-transistors operate in a known manner in response to electrical signals provided to them via the respective PCBs 442,402. The LED 446 in the docking station is physically arranged so that its light emissions are received only by the photo-transistor 408 in the monitoring device 310, and the LED 410 in the monitoring device 310 is physically arranged so that its light emissions are received only by the photo-transistor 448 in the docking-station 340 when the monitoring device 310 is docked in the docking station 340. The use of optical transducers 320,342 eliminates adverse effects due to surrounding RF fields, such as might occur in an operating room, as described above.

As described with reference to FIG. 2, the LEDs and photo-transistors may be replaced or augmented with a small RF antenna, possibly in the form of a strip line, shielded in a known manner. The use of an RF link simplifies the circuitry required in the central-location 100 because needs only a single RF transceiver rather than an RF transceiver and an optical transceiver. With proper shielding, adverse effects of interfering RF signals may be minimized.

In operation, when the monitoring device 310 is docked in the docking station 340, indicated by dashed arrows in FIG. 4*a* and illustrated in FIG. 4*c*, an alternating current is supplied from the power supply 200 to the primary windings (not shown) in PCB 442 surrounding the central pole 462 in the primary 344 of the split transformer. This alternating current induces a magnetic field within the armature formed by the primary and secondary ferrite armatures, 444,404. As described above, the faces of the central poles 462,422, and peripheral poles 464,424 and 466,426, are aligned and separated only by thin layers of plastic. A complete magnetic circuit is, therefore, formed by the central poles 462,422 and the peripheral poles 464,424 and 466,426. A secondary current is thereby induced in the secondary winding (also not shown) in the PCB 402 in the monitoring device 310. This secondary current is supplied to the power supply 316 to power the monitoring device 310 and recharge the battery 318. Simultaneously, the alignment of the LED 446 with photo-transistor 408 and the LED 410 with photo-transistor 448 provides full duplex data communication between the monitoring device 310 and docking station 340.

Because of the relatively wide area of the PCBs 442,402 around the central poles 462,422, a relatively large number of windings may be fabricated around those poles. Also, this large primary winding area facing and close to its corresponding congruent secondary winding maximizes coupling and minimizes losses. In addition, because of the relatively small separation of the faces of the poles 462,422; 464,424 and 466,426, there is only minor leakage of magnetic flux. This leads to increased efficiency of operation, on the order of 85%, of the split transformer illustrated in FIG. 4 compared to prior split transformers. A compact, efficient configuration can be realized using these principles.

What is claimed is:

1. A communications system suitable for use in a portable patient monitoring network, comprising:

circuitry for providing a first electrically isolated bidirectional communications channel between a portable device and a central controller via a selected docking station and a network, said central controller being in communication with a plurality of different remotely located docking stations via a network and an individual portable device operates in a first mode when docked in a docking station and a second mode when undocked;

circuitry for providing a second electrically isolated bidirectional communications channel directly between the portable device and the central controller; and circuitry for establishing communications via the first communications channel when the portable device is docked to the selected docking station in the first mode and establishing communications via the second communications channel in the second mode when undocked.

2. The system of claim 1 wherein said portable patient monitoring network includes, a central controller bidirectionally coupled to the network; one or more docking stations each bidirectionally coupled to the network; and one or more portable devices each capable of docking with a selected one of the docking stations.

3. The system of claim 2 wherein the circuitry for providing the first communications channel comprises:

circuitry in the docking station for receiving network-compatible data from the network; and circuitry in the portable device for extracting data from the received network-compatible data.

4. The system of claim 2 wherein the circuitry for providing the second communications channel comprises:

circuitry in the central controller for generating network-compatible data according to a predetermined network protocol and transmitting this data wirelessly to the portable device; and circuitry in the portable device for receiving the network-compatible data from the central controller and extracting data from the received network-compatible data.

5. The system of claim 2 wherein each of the portable devices transmits patient monitoring data to the central controller and the central controller transmits data for controlling the operation of the portable device to the portable device.

6. The system of claim 2 wherein:

the network transmits data formatted according to a predetermined network-compatible protocol; and each portable device comprises circuitry for generating data according to the network-compatible protocol.

7. The system of claim 6 wherein the selected network protocol is selected from the group consisting of internet protocol (IP), universal serial bus (USB), I.E.E.E. network protocol, and local area network (LAN) protocol.

8. The system of claim 1 wherein said circuitry for establishing communications automatically selects and establishes a particular communication channel in response to at least one of, (a) docking of a portable patient monitor device, (b) detection of loss of communication on an established communication channel and (c) detection of an absence of a particular communication channel.

9. The system of claim 1 wherein the circuitry for providing the second communications channel further comprises a standalone transceiver, coupled to the network, for receiving the network-compatible data from the portable device and the received network-compatible data on the network.

10. The system of claim 1 wherein the circuitry for providing the second communications channel further comprises a standalone transceiver, coupled to the network, for receiving network compatible data from the central controller and transmitting this data wirelessly to the portable device.

11. In an electrically isolated portable patient monitoring network comprising: a central controller; one or more remotely located docking stations each coupled in communications with the central controller via a network; and one or more portable devices each capable of docking with a selected one of the docking stations; a communications system comprising:

circuitry for providing a first electrically isolated communications channel from the portable device to the central controller via the selected docking station;

circuitry for providing a second electrically isolated communications channel from the portable device directly to the central controller; and circuitry for establishing communications via the first communications channel when the portable device is docked to the selected docking station and establishing communications via the second communications channel when undocked.

12. The system of claim 11 wherein a data transducer in each docking station is hardwire coupled to the central controller.

13. The system of claim 11 wherein:

a transducer in each docking station comprises a wireless communications antenna; and the transducer in each portable device comprises a wireless communications antenna arranged to communicate with the wireless communications antenna in the selected docking station when the portable device is docked with the selected docking station.

14. The system of claim 1 wherein:

the central controller comprises a wireless communications antenna; and the circuitry in each portable device for providing the second communications channel comprises an additional wireless antenna arranged to exchange data with the antenna in the central controller when the portable device is not docked with any of the docking stations.

15. The system of claim 14 wherein:

the central controller comprises a wireless communications antenna; and the wireless communications antenna in the portable device is further arranged to exchange data with the antenna in the central controller when the portable device is not docked with any of the docking stations.

16. The system of claim 11 wherein:

the central controller comprises a wireless communications antenna; and the circuitry in each portable device for providing the second communications channel comprises a wireless antenna arranged to exchange data with the antenna in the central controller when the portable device is not docked with any of the docking stations.

17. The system of claim 11 wherein the circuitry for establishing communications is coupled to the circuitry providing the first communications channel and comprises circuitry that determines that the portable device is docked to a selected docking station when data is detected on the first communications channel.

18. The system of claim 11 wherein:

each of the docking stations further comprises an electrically isolated power coupler;

each of the portable devices further comprises an electrically isolated power coupler arranged to receive power from the power coupler in the selected docking station when the portable device is docked to the selected docking station; and the circuitry for establishing communications comprises:

circuitry in each portable device, coupled to the power coupler in the portable device, that determines that the portable device is docked to a selected docking station when received power is detected; and circuitry in each docking station, coupled to the power coupler in the docking station, that determines that the portable device is docked to the docking station when a load is detected on the power coupler in the docking station.

* * * * *